(12) United States Patent
Webster (10) Patent No.: US 6,666,884 B1
(45) Date of Patent: Dec. 23, 2003

(54) BIFURCATION STENT AND DELIVERY SYSTEMS

(76) Inventor: Mark Wilson Ian Webster, 19 Windmill Road, Mt. Eden, Auckland (NZ)

( * ) Notice: Subject to any disclaimer, the term of this patent is extended or adjusted under 35 U.S.C. 154(b) by 0 days.

(21) Appl. No.: 09/831,568

(22) PCT Filed: Nov. 10, 1999

(86) PCT No.: PCT/NZ99/00190

§ 371 (c)(1),
(2), (4) Date: Jul. 27, 2001

(87) PCT Pub. No.: WO00/27463

PCT Pub. Date: May 18, 2000

(30) Foreign Application Priority Data

Nov. 11, 1998  (NZ) ................................................ 332725
May 31, 1999  (NZ) ................................................ 335530

(51) Int. Cl.$^7$ .................................................. A61F 2/06
(52) U.S. Cl. ...................... 623/1.35; 623/1.1; 623/1.37
(58) Field of Search ................................. 623/1.1, 1.35, 623/1.37, 1.16

(56) References Cited

U.S. PATENT DOCUMENTS

| | | | | |
|---|---|---|---|---|
| 4,994,071 A | | 2/1991 | MacGregor | 606/194 |
| 5,669,924 A | * | 9/1997 | Shaknovich | 623/1.35 |
| 5,676,696 A | * | 10/1997 | Marcade | 623/1.1 |
| 5,720,735 A | | 2/1998 | Dorros | 604/284 |
| 6,254,593 B1 | * | 7/2001 | Wilson | 623/1.35 |

FOREIGN PATENT DOCUMENTS

| | | | | |
|---|---|---|---|---|
| WO | WO 95/16406 | 6/1995 | | A61F/2/06 |
| WO | WO 96/14028 | 5/1996 | | A61F/2/06 |

OTHER PUBLICATIONS

International Search Report PCT/NZ 99/00190.

* cited by examiner

*Primary Examiner*—Julian W. Woo
(74) *Attorney, Agent, or Firm*—Myers Bigel Sibley & Sajovec

(57) ABSTRACT

A bifurcation stent (1) having a closed terminus (4) and two angled apertures (5, 6) at its distal end (3). The bifurcation stent may be a balloon-inflated stent, or a self-expanding stent. The delivery systems for the stent employ a guide wire through each aperture of the stent.

7 Claims, 12 Drawing Sheets

BIFURCATION STENT AND DELIVERY SYSTEMS

CROSS-REFERENCE TO RELATED APPLICATIONS

The present application is a U.S. national phase application of PCT International Application No. PCT/NZ 99/00190, having an international filing date of Nov. 10, 1999 and claiming priority to New Zealand Application Nos. 332725 filed Nov. 11, 1998 and 335530 filed May 3, 1999. The above PCT International Application was published in the English language and has International Publication No. WO 00/27463.

FIELD OF THE INVENTION

The present invention relates to apparatus for treating coronary or other vascular bifurcation lesions, and in particular to a stent used to treat the upstream vessel and/or the bifurcation region itself, and delivery systems to deploy this stent.

BACKGROUND TO THE INVENTION

Stenotic lesions which develop in vascular disease commonly occur at bifurcations, where a parent vessel divides into two branch vessels. Such lesions are difficult to treat particularly as a result of the geometry of the bifurcation region itself, the fact that bifurcation lesions come in many shapes and forms and the fact that there can be many configurations of downstream vessels; the angles between the parent and down stream vessels can vary considerably.

Vascular stents are a typical form of treatment of such lesions. There are two common forms of stent and deployment method:

(i) self-expanding stents, which are typically retained in their constrained form by a sheath or sleeve which is withdrawn to enable the stent to expand;

(ii) balloon expanded stents, which involve the mounting of the stent upon a balloon which is inflated to deploy the stent when the stent is located in the region to be treated.

Both forms of stent employ the use of guide wires to help locate the stent in the region to be treated before deployment.

Most stent designs in use are essentially cylindrical in shape with single transverse apertures at each end. When these stents are used in the generally angled region of a bifurcation then there is less than optimal vessel wall coverage as well as stent distortion particularly at the site of vessel bifurcation.

It is an object of the present invention to provide a stent which overcomes or at least ameliorates some of the above-mentioned disadvantages or to at least provide the public with a useful choice.

Other objects of the invention may become apparent from the following description which is given by way of example only.

SUMMARY OF THE INVENTION

According to a first aspect of the invention there is provided a bifurcation stent open at a proximal end, having a closed terminus at a distal end, and apertures adjacent the closed terminus and at an angle in relation to the longitudinal axis of the stent.

Preferably the apertures include a first aperture and a second aperture substantially on opposite longitudinal sides of the stent.

Preferably the first aperture and the second aperture may have a common angle in relation to the longitudinal axis of the stent.

Preferably the bifurcation stent may be a self-expanding stent, or alternatively a balloon-inflated stent.

According to a second aspect of the invention there is provided a bifurcation stent adapted for use in an upstream vessel at a bifurcation capable of being positioned at the carina of the bifurcation substantially without extending into either downstream vessel.

According to a third aspect of the invention there is provided a stent delivery system adapted to deliver the balloon-inflated bifurcation stent of the first aspect of the invention including a balloon mechanism, the balloon mechanism forming one or more head portion at a distal end adapted to engage an aperture of the bifurcation stent, and the stent delivery system further including one or more lumen through the balloon mechanism and exiting from the or each head portion.

According to a fourth aspect of the invention there is provided a method of deploying a balloon inflatable stent at a bifurcation, including the steps of:

mounting a balloon deployed stent having a closed terminus at a distal end and first and second apertures adjacent the closed terminus on a balloon mechanism having a first head portion extending into the first aperture and a second head portion extending into the second aperture, a first guidewire passing through a lumen in the balloon mechanism exiting from the first head portion and a second guidewire passing through a lumen in the balloon mechanism and exiting from second head portion;

locating the first guidewire in a parent vessel with the first distal end of the guidewire extending beyond an ostium of a first downstream vessel;

locating the second guidewire in the parent vessel with the first distal end of the guidewire extending beyond an ostium of second downstream vessel;

advancing the balloon-inflatable stent along the guidewires in the parent vessel until the closed terminus abuts a carina at the bifurcation, with the first head portion of the balloon mechanism aligned with the ostium of the first downstream vessel and second head portion of the balloon mechanism aligned with the ostium of the second downstream vessel;

inflating the balloon mechanism to expand the stent, the first and second head portions of the balloon mechanism extending into their corresponding ostia.

According to a fifth aspect of the invention there is provided a stent delivery system adapted to deliver the self-expanding bifurcation stent of the first aspect of the invention, the system including an outer delivery sleeve adapted to constrain the self-expanding stent in restricted form and enable expansion of the stent by withdrawal of the sleeve; one or more lumens passing through the delivery sleeve and extending at least to the distal end of the delivery sleeve, the or each lumen adapted to house one or more guidewires and enable a guidewire to exit each aperture of the stent; and said sleeve not prohibiting the passage of the or each lumen and/or guidewire through the aperture.

Preferably the stent delivery system may further include locating means at the distal end of the delivery sleeve, the locating means adapted in use to position the closed terminus of the stent substantially opposed to the carina of the bifurcation.

According to a sixth aspect of the invention there is provided a method of deploying a self-expanding bifurcation stent, the method including the steps of:

housing an unexpanded bifurcation stent having a closed terminus at a distal end and first and second apertures adjacent to the closed terminus, in an outer delivery sleeve, the sleeve not occluding the first and second apertures, mounting the unexpanded stent and its sleeve on first and second guidewires passing through one or more lumens through the delivery sleeve and extending at least to the distal end of the delivery sleeve, such that a guidewire exits each aperture;

locating the first guidewire in a parent vessel with its first distal end extending beyond an ostium of a first downstream vessel;

locating the second guidewire in a parent vessel with its first distal end extending beyond an ostium of a second downstream vessel;

advancing the stent and sleeve along the guidewires until the closed terminus of the stent is substantially opposed to the carina of the bifurcation, the apertures of the stent being aligned with the ostia of the downstream vessels;

deploying the stent by withdrawal of the delivery sheath, the apertures expanding and aligning with the ostia of the downstream vessels.

Preferably the method may further include the step of engaging locating means at the distal end of the delivery sleeve on the carina of the bifurcation prior to deploying the stent.

According to a seventh aspect of the invention there is provided an arrangement of stents in a bifurcation including the bifurcation stent of the first aspect of the invention located in the upstream vessel of the bifurcation with its closed terminus substantially opposed to the carina and at least one aperture aligned with an ostium of one downstream vessel; and at least one tubular stent located in a downstream vessel with a proximal aperture substantially aligned with the aperture of the bifurcation stent.

Other aspects of the invention may become apparent from the following description which is given by way of example only and with reference to the accompanying drawings.

BRIEF DESCRIPTION OF THE DRAWINGS

The invention will now be described by way of example only and with reference to the drawings in which.

DETAILED DESCRIPTION OF THE INVENTION

Figure 1:
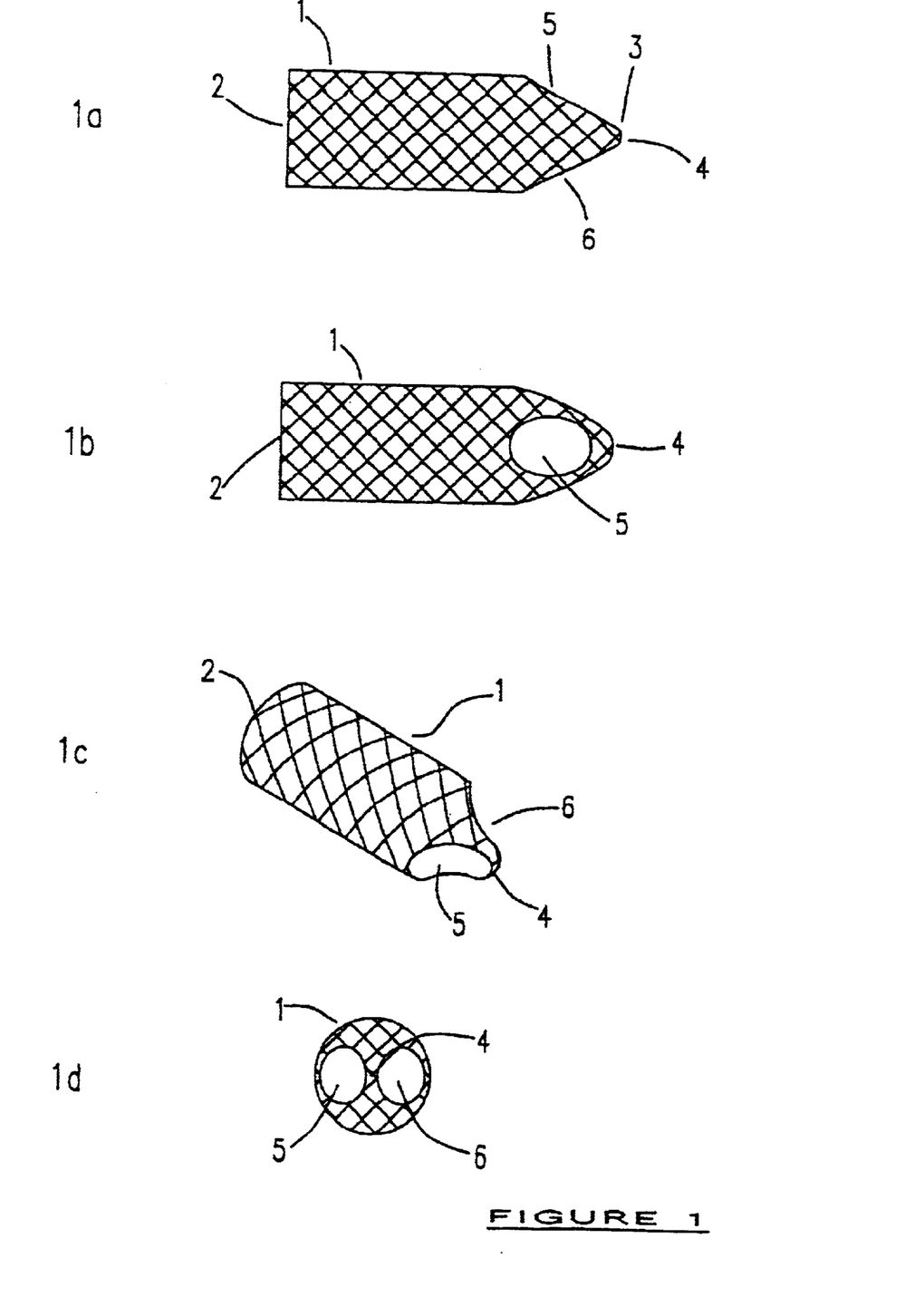
FIG. 1: shows schematic plan, side, perspective and end views of a deployed stent according to one aspect of the invention.

With reference to FIG. 1 there is provided a plan view (1a), side view (1b), perspective view (1c), and end view (1d), of a bifurcation stent of the invention. The stent, shown generally as 1, is of a generally cylindrical geometry, having a proximal end, 2 and a distal end 3. At the distal end the stent is provided with a terminal portion which essentially runs transverse the longitudinal axis if the stent and is hereinafter referred to as a closed terminus 4, and two angled apertures 5, 6. The stent of FIG. 1 is a fully deployed stent. It will be appreciated that the general geometry of the stent shown in FIG. 1 will not be typical of unexpanded stents prior to deployment in the bifurcation region of a blood vessel.

Figure 2:
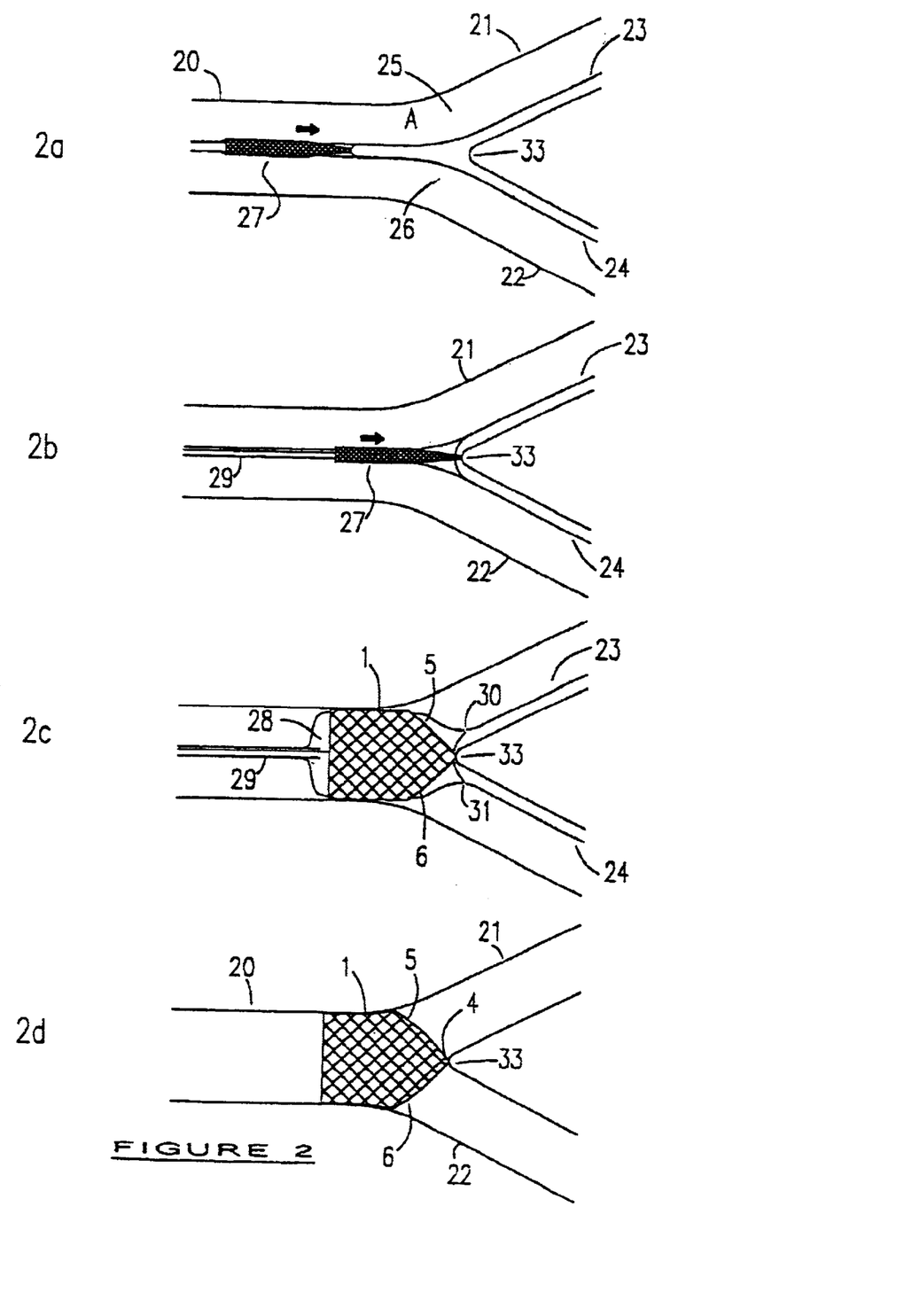
FIG. 2: shows the process of deployment of the stent of FIG. 1 by a balloon inflation method.

FIG. 2 illustrates the locating and deployment of a stent of FIG. 1 employing a balloon expanded delivery system. The zone of the bifurcation A is formed where the parent vessel 20 branches into two downstream vessels 21, 22. Initially the two guidewires, 23 and 24 are inserted down and along the parent vessel 20. At the bifurcation zone A, the first guidewire 23 is manipulated so that its distal end enters the ostium 25 of vessel 21, and is advanced into vessel 21. The second guidewire 24, is manipulated so that its distal end enters the ostium 26 of vessel 22, and is advanced into vessel 22.

The stent and delivery system, shown generally as 27 comprise a delivery balloon 28, through which runs a lumen 29 for accommodating the guidewires 23, 24. FIG. 2 shows a single lumen accommodating both guidewires which separate at the distal end, but it will be appreciated that two lumens may exist, each accommodating a separate guidewire. The balloon 28 has two bulges forming heads 30 and 31, at the distal end of the balloon. The guidewires 23, 24 emerge from the balloon at the heads of the balloon 30, 31 respectively. The stent 1 is mounted on the outside of the balloon 28, and the heads of the balloon 30, 31 may extend slightly through the apertures 5, 6 of the stent 1.

As shown in FIGS. 2a and 2b, the stent and delivery system 27 are advanced along the guidewires 23, 24, until the closed terminus 4 of the stent reaches the carina 33 of the bifurcation zone A. As the delivery system reaches the bifurcation zone A, the apertures 5, 6 of the stent 1 are forced to align with the ostia 25, 26. Once the closed terminus 4 is in place at the carina 33, the balloon 28 is inflated to expand the stent 1, as shown in FIG. 2c. Once the stent 1 is fully expanded the balloon 28 and guidewires 23, 24 are removed leaving the expanded stent 1 in place in the bifurcation zone A.

As there is less overall metal at the distal end 3 of the stent 1, as a result of the presence of the apertures 5, 6, stent expansion will tend to occur at the distal end first. This will assist in optimal alignment of the apertures 5, 6 with the ostia 25, 26, and in retaining the closed terminus proximal to the carina 33.

Figure 3:
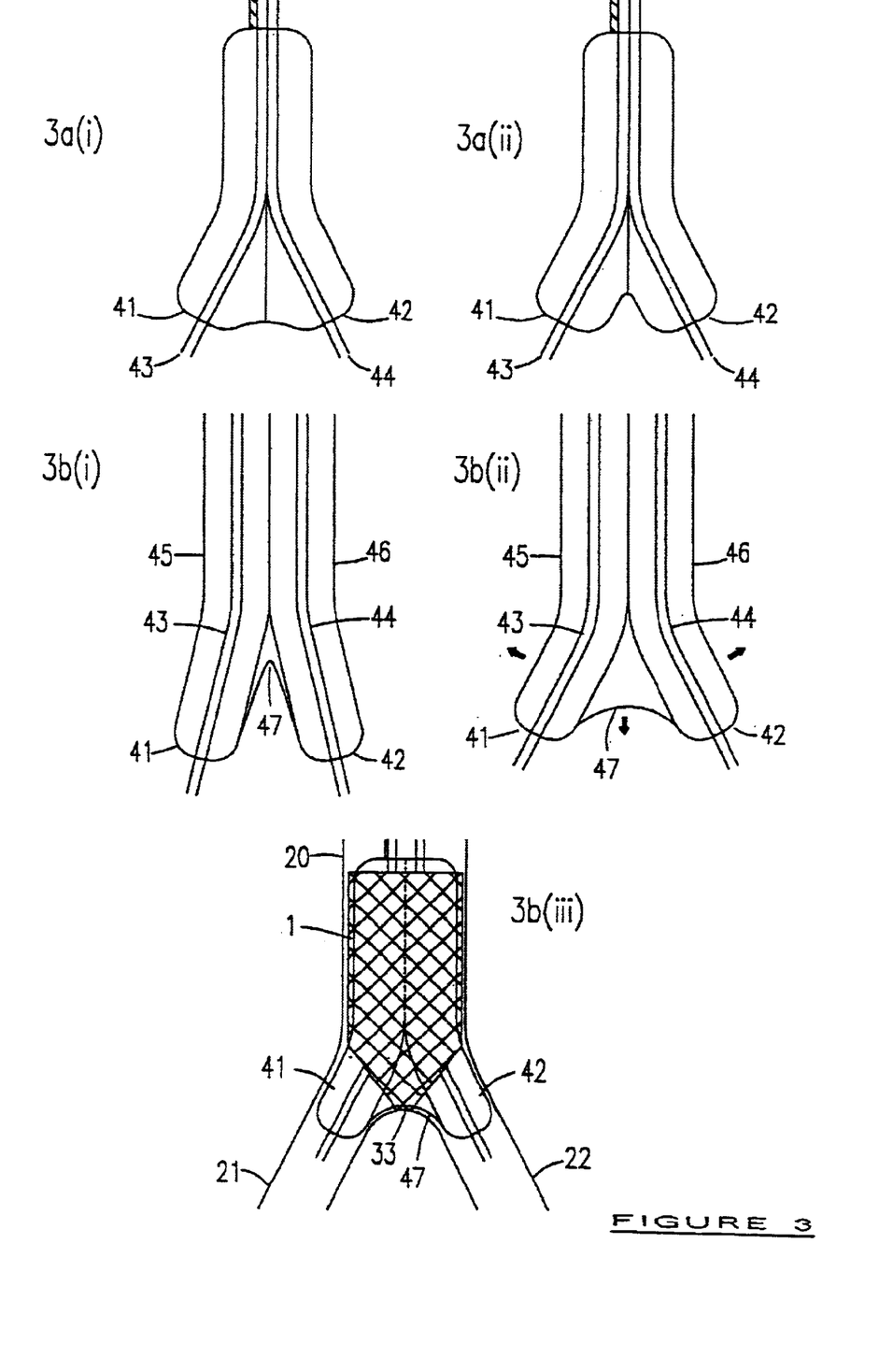
FIG. 3: shows variations of balloon configuration suitable for use in balloon deployment of a stent according to the invention.

FIG. 3 shows different possible configurations for the balloon of the expanding stent delivery system. FIGS. 3a(i) and (ii) show different variations of a balloon which diverges at its distal end to form two distinct heads 41, 42 through which the lumens 43, 44 emerge.

FIGS. 3b(i), (ii) and (iii) show an alternative balloon configuration which incorporates two balloons 45, 46, in a "kissing" formation, which are attached together (by adhesive or heat bonding, for example) along much of their length and diverge at their distal ends. Each balloon 45, 46 contains a separate lumen 43, 44. There also may be a flexible hinge 47, joined to the balloons, between the heads 41, 42 of the balloon. This hinge 47 may increase the manoeuvrability of the heads 41, 42, and aid in location of the closed terminus 4 against the carina 33.

FIGS. 3c(i), (ii) and (iii) show a balloon having two separate lumens 43, 44 which run the length of the balloon generally side by side, but which diverge at the distal end of the balloon, exiting at the centres 48, 49 of the balloon heads 41, 42. An alternative configuration is provided in FIGS. 3d(i) and (ii) wherein the lumens 43, 44 emerge from the heads 41, 42 at off-centre positions.

FIG. 3e illustrates an alternative configuration with a single lumen 49 at the proximal end of the balloon, which separates to form two lumens 50, 51 at the distal end of the balloon.

FIG. 3f illustrates a further alternative configuration having an external lumen 52 in addition to the internal lumen 53. With this design only one aperture of the stent is aligned accurately with the ostium of a downstream branch during balloon inflation.

Figure 4:
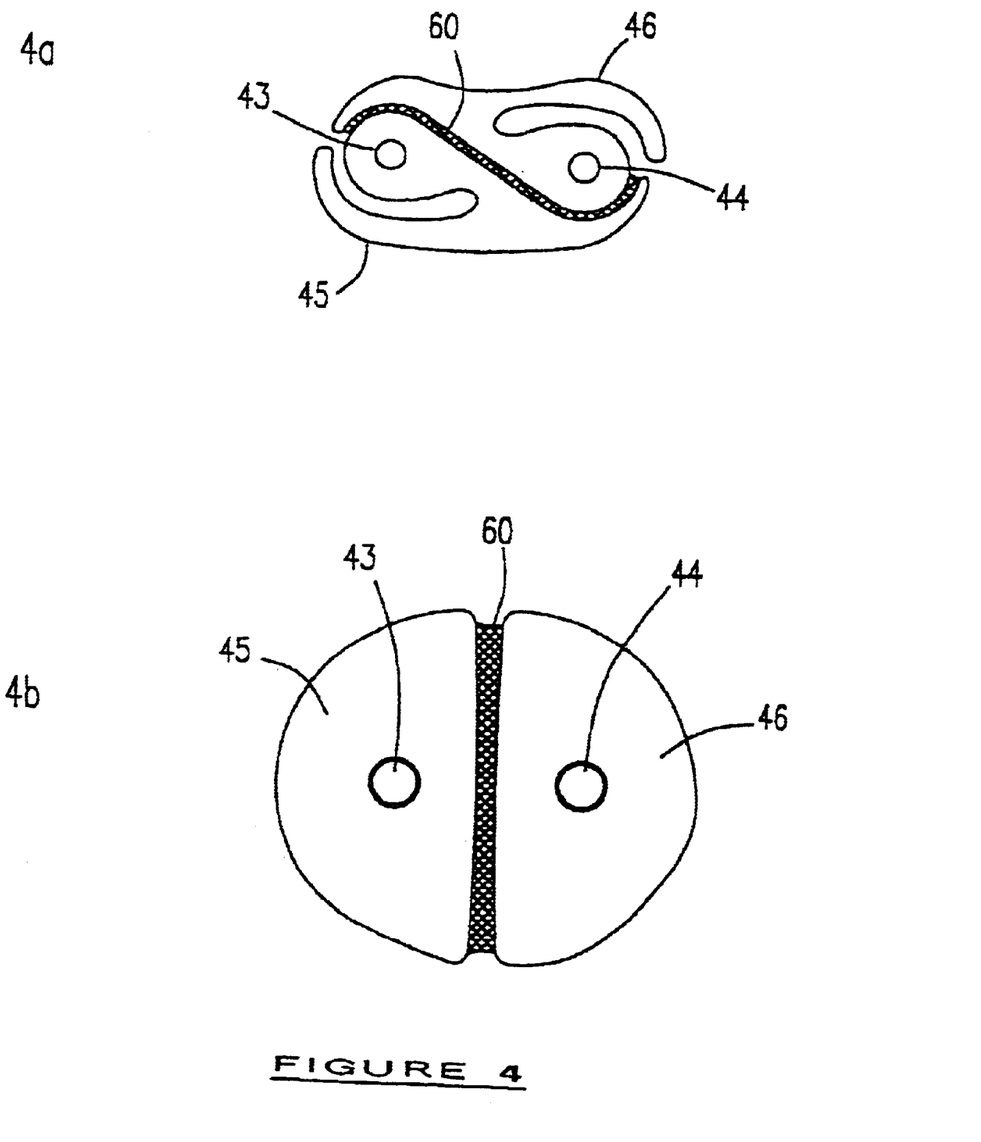
FIG. 4: shows an alternative double delivery balloon for use in balloon deployment of a stent according to the invention.

FIG. 4 illustrates in cross-section, a modification to a double delivery balloon, such as that illustrated in FIG. 3b, in order to maintain a generally circular profile of the balloon in inflation. The separate balloons 45, 46 have separate lumens 43, 44 running the length of the balloons. These balloons are bonded together using a suitable adhesive 60 or by other means. FIG. 4a shows this modified balloon system in an un-inflated state; FIG. 4b in the inflated state.

Figure 5:
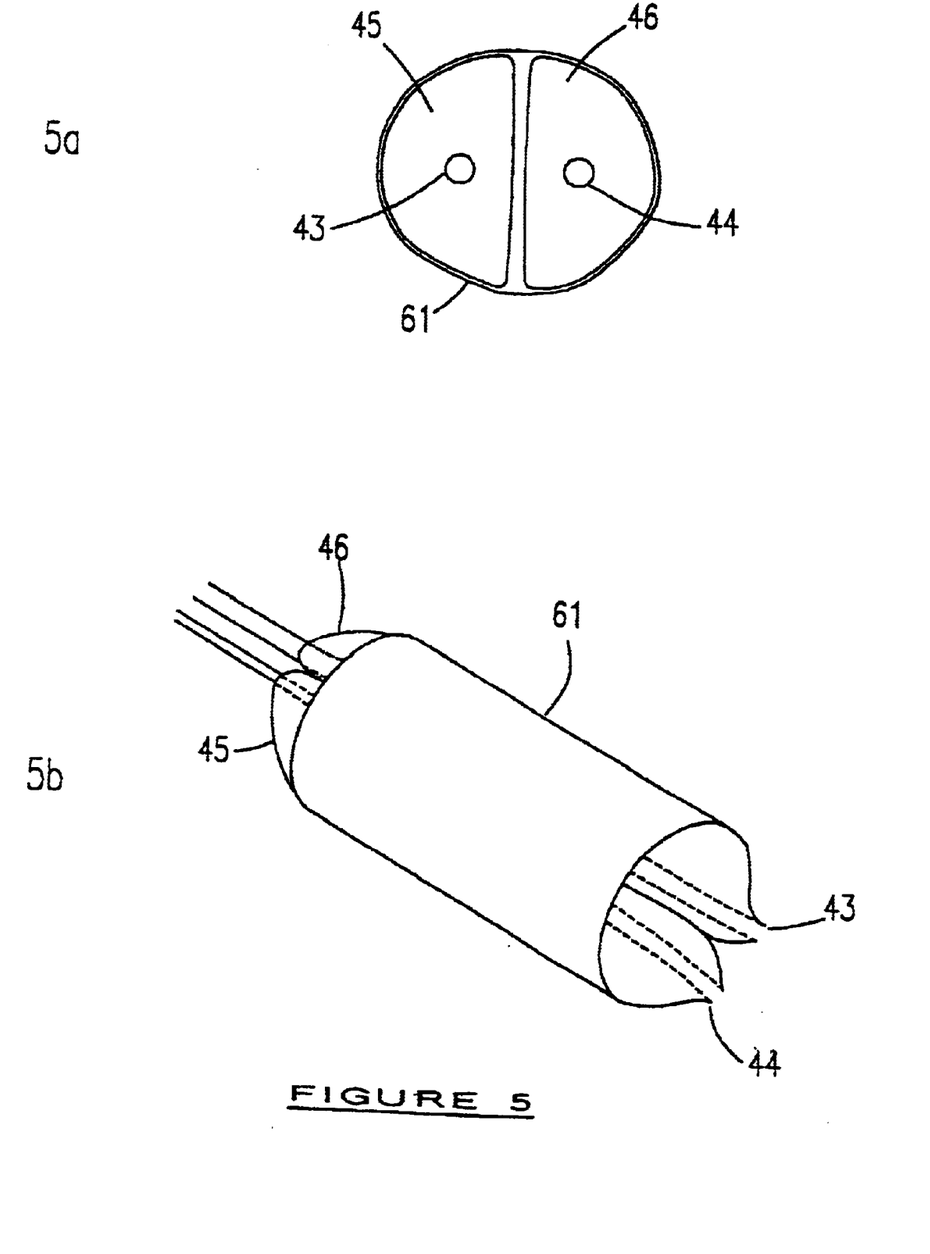
FIG. 5: shows a modified double delivery balloon for use in deployment of a stent according to the invention.

FIG. 5 provides cross section (5a) and perspective (5b) views of an alternative modified double delivery balloon, such as that illustrated in FIG. 3b, in order to maintain a generally circular profile during inflation of the balloon. The separate balloons 45, 46 have separate lumens 43, 44 running the length of the balloons. An outer sleeve 61 is also used to constrain the geometry of the double balloon as it is expanded.

Figure 6:
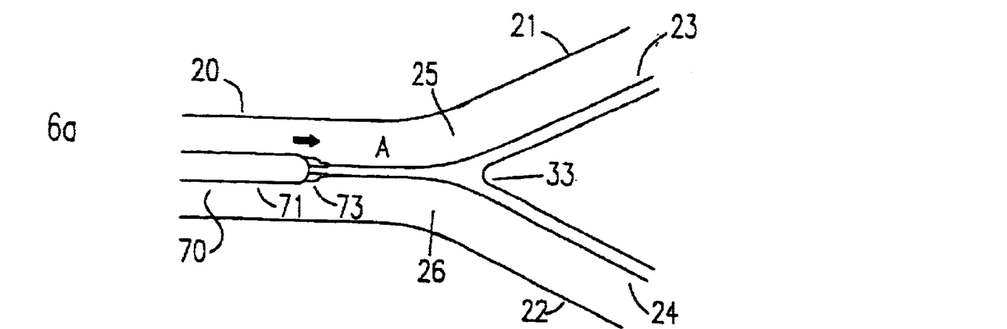
FIG. 6: shows the deployment of a self-expanding stent according to another aspect of the invention.

FIG. 6 illustrates the locating and deployment of a stent by an alternative method employing a self-expanding stent and delivery system. The zone of the bifurcation A exists where the parent vessel 20 branches into two downstream vessels 21, 22. Initially the two guidewires 23, 24 are inserted down and along the parent vessel 20. At the bifurcation zone A guidewire 23 is manipulated so that its distal end enters the ostium 25 of vessel 21 and is advanced along vessel 21. Guidewire 24 is manipulated so that its distal end enters the ostium 26 of vessel 22, and is advanced along vessel 22.

The stent and delivery system, shown generally as 70 comprises an outer delivery sleeve 71 within which two lumen (not shown), housing the guidewires 23, 24 are contained. The self-expanding stent 72, is also contained within the sleeve 71 in its restricted form. The guide wires 23, 24, within the lumens, run within the stent 72 and emerge at the distal end through apertures 5, 6.

FIG. 6 also illustrates a locating means, generally 73, which may be used to facilitate positioning of a stent of the present invention. The locating means 73 comprises a first jaw 74 and a second jaw 75 through which the guide wires 23, 24 emerge. The jaws 74, 75 are able to engage with the carina 47, thereby helping to keep the stent in place, adjacent to the carina 47 when deployed.

The stent and delivery system, generally 70, are advanced along the guidewires 23, 24 as shown in FIG. 6a, until the closed terminus 4 of the stent 72 meets the carina 33 of the bifurcation zone A, (FIG. 6b). As the delivery system reaches the bifurcation zone A, the jaws 74, 75 of the locating means 73 are forced to diverge, one jaw 74 towards the ostium 25, and the other jaw 75 towards the ostium 26, of the downstream vessels 21, 22, thereby engaging about the sides of the carina 33. This forces the apertures 5, 6 of the stent 72 to align with the ostia 25, 26. Once the closed terminus 4 is in place at the carina 33, the sleeve 71 is carefully withdrawn, (FIG. 6c). The stent 72 expands into position, being held adjacent to the carina 33 by the jaws 74, 75. Once the expansion is complete the sleeve 71, guidewires 23, 24 and locating means 73 are removed to leave the stent in place in the bifurcation zone A, (FIG. 6d). The apertures 5, 6 of the stent are aligned with the ostia 25, 26 of the downstream vessels.

Figure 7:
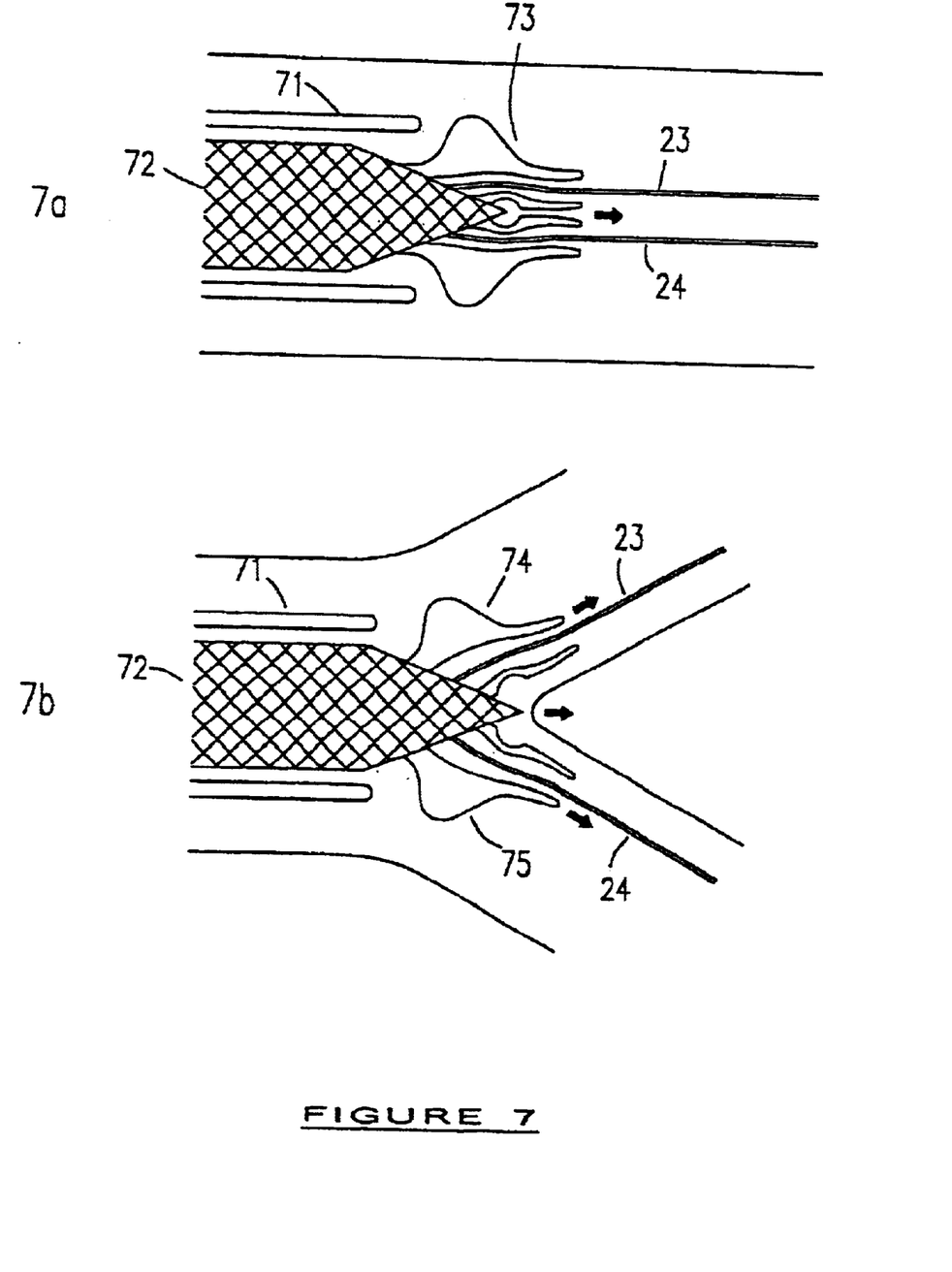
FIG. 7: shows a locating means of the delivery device according to a preferred embodiment of one aspect of the invention.

One particular configuration of the locating means 73 is shown in FIG. 7. This shows the guidewires 23, 24 extending out of the distal ends of each jaw 74, 75.

Figure 8:
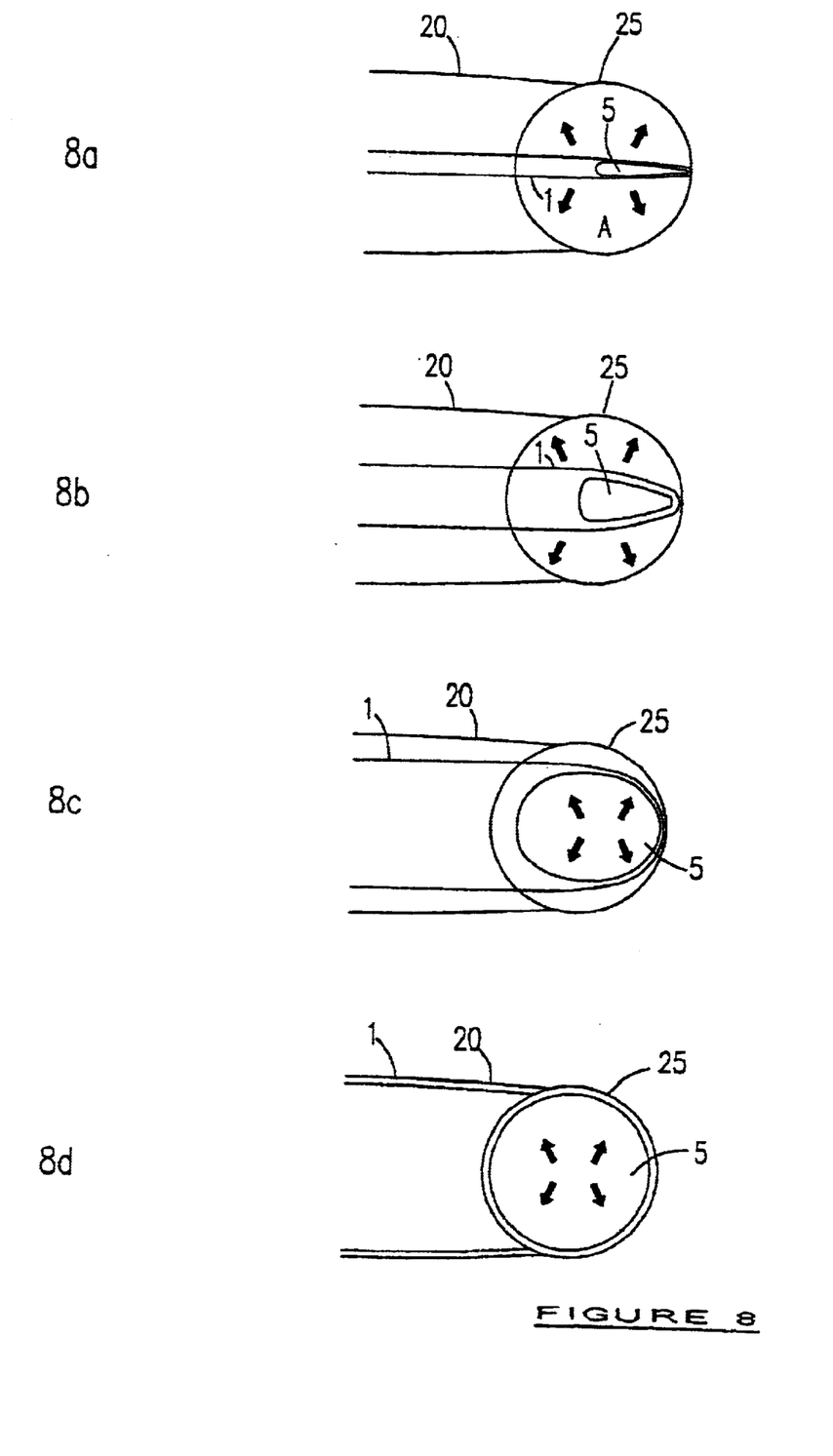
FIG. 8: shows a view from a downstream branch vessel of stent deployment.

FIG. 8 shows a view to the bifurcation zone A, through the ostium 25 (or 26) of a downstream vessel 21 (or 22), of a stent 1 being deployed by either balloon-inflation or self-expanding delivery systems (not shown). As the stent 1 expands (FIG. 8b) the aperture 5 (or 6) of the stent 1 also expands so that in the fully expanded state of FIG. 8d it substantially covers the area of the ostium 25. Differing sizes of stent in comparison with ostia may result in only partial coverage of an ostium by the aperture, but these will be substantially aligned.

The result of deployment of the stent by either the balloon expanding delivery system, or the self-expanding stent and delivery system, or by any other suitable deployment system as can be envisaged by one skilled in the art, will be that the stent 1 is located in the bifurcation zone A such that the apertures 5, 6 are aligned with, and at least partially cover, the ostia 25, 26, and the closed terminus 4 is opposed the carina 33.

This configuration has a number of advantages.

The deployed stent has an "anatomic" design, conforming to the shape of the bifurcation zone, immediately upstream of the bifurcation. The deployed stent has optimal wall coverage with no stent distortion, unlike generally tubular stents when employed in bifurcation zones.

The apertures of the stent are aligned with the ostia of both downstream branches over a wide range of angles between the downstream branches. As a result this arrangement allows easy access to the downstream branches for treatment if required. This is not the case for tubular stents of the prior art which use side holes for stent deployment in downstream vessels, resulting in sharp angles for balloons or stents to negotiate.

As the stent does not extend into the downstream vessels and the apertures are aligned with the ostia of these vessels, stents of standard design 90 as known in the industry may be used to treat one or both downstream branches.

Figure 9:
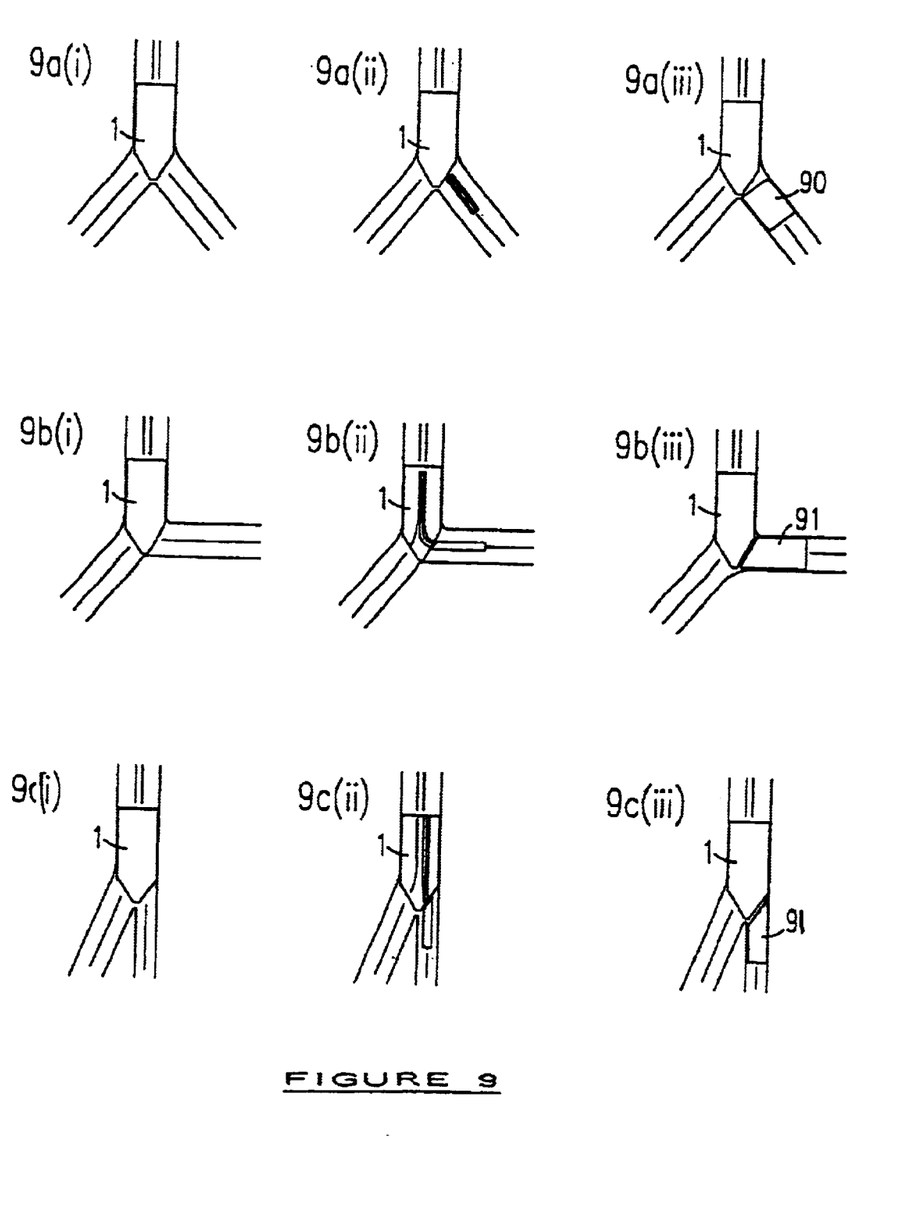
FIG. 9: shows examples of configurations of a stent arrangement at a bifurcation using a stent and method of deploying stents of the invention.

FIG. 9 illustrates that as the angles between the downstream branches become more extreme then tubular stents with an angled proximal end 91 could be employed for treatment of the branch vessels.

Figure 10:
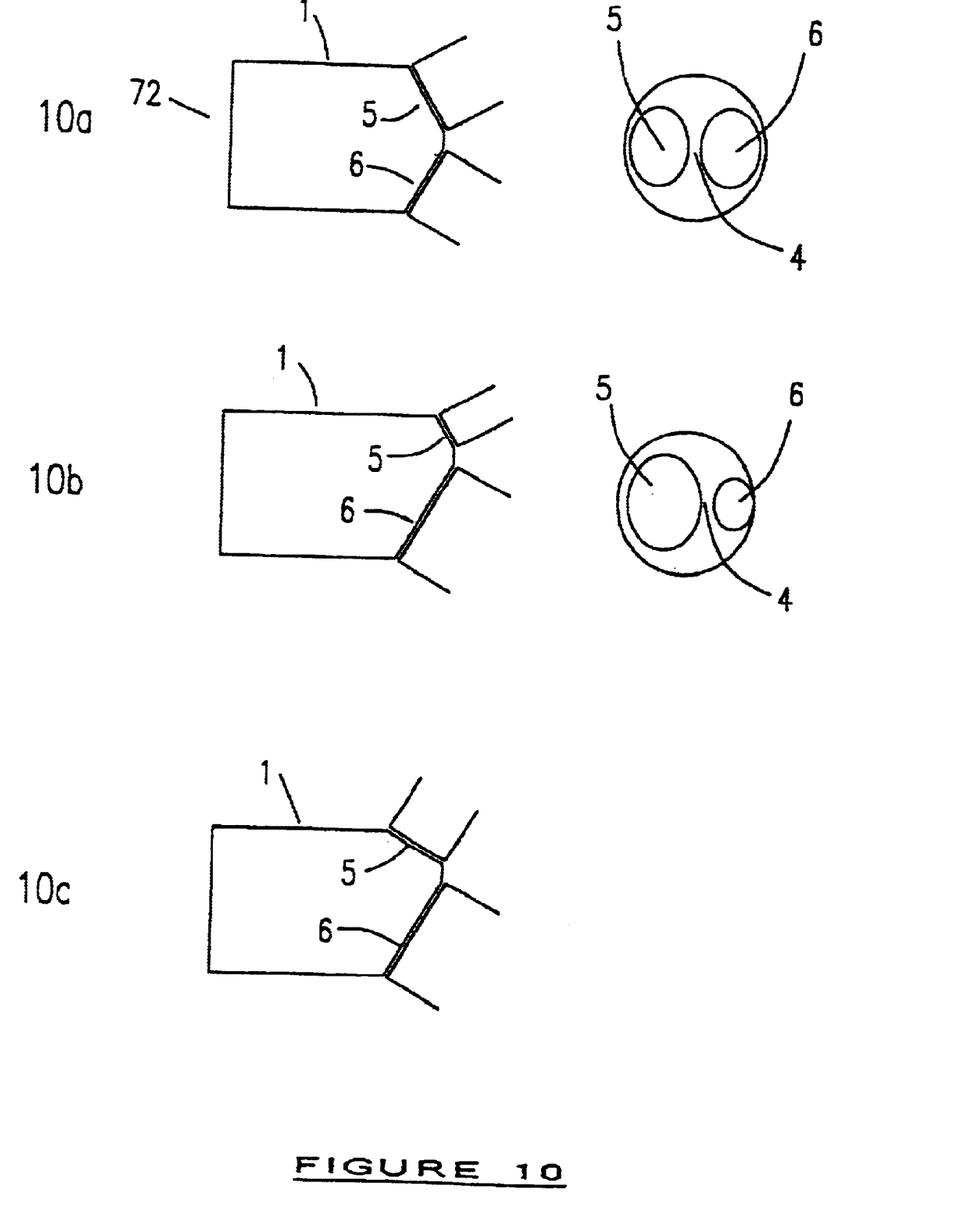
FIG. 10: shows examples of variation in size and angle of the apertures of a bifurcation stent of the invention.

In order to more precisely fit the geometry of a bifurcation and downstream vessels the configuration of a stent of the present invention may be altered, as shown in FIG. 10, by altering the positions, sizes and angles of the apertures 5, 6. These modifications retain the essential feature of a closed terminus 4. An asymmetrical stent of this type may be used with downstream stents of different dimensions as shown in FIGS. 10a, b and c.

As is known in the prior art, the proximal portion of the balloon-expanded or self-expanding stent delivery systems may have a double over-the-wire configuration, a double monorail configuration, or a combination over-the-wire monorail configuration.

Where in the foregoing description reference has been made to elements or integers having known equivalents, then such equivalents are included as if they were individually set forth.

Although the invention has been described by way of example and with reference to particular embodiments, it is to be understood that modifications and/or improvements may be made without departing from the scope or spirit of the invention.

What is claimed is:

1. A stent capable of operating as a bifurcation stent having a body comprising a proximal end having an opening, and a distal end having a closed terminus at the distalmost point and two apertures, the apertures separated by the closed terminus, the apertures extending from the closed terminus to a position between the proximal and distal ends at an angle in relation to the longitudinal axis of the stent.

2. A stent according to claim 1, wherein the apertures comprise a first and a second aperture positioned substantially opposite each other on the body.

3. A stent according to claim 2, wherein the first aperture and the second aperture have a common angle in relation to the longitudinal axis of the stent.

4. A stent according to claim 1, which is a self-expanding stent.

5. A stent according to claim 1, which is a balloon-inflated stent.

6. A stent according to claim 1, adapted for use in an upstream vessel at a bifurcation capable of being positioned at the carina of the bifurcation substantially without extending into either downstream vessel.

7. A stent according to claim 6, wherein the apertures, in use, empty into the downstream vessels.

* * * * *